US008770050B2

(12) United States Patent (10) Patent No.: US 8,770,050 B2
Clark (45) Date of Patent: Jul. 8, 2014

(54) METHOD OF MEASURING MICRO- AND NANO-SCALE PROPERTIES

(76) Inventor: Jason Vaughn Clark, Lafayette, IN (US)

(*) Notice: Subject to any disclaimer, the term of this patent is extended or adjusted under 35 U.S.C. 154(b) by 1555 days.

(21) Appl. No.: 11/378,596

(22) Filed: Mar. 17, 2006

(65) Prior Publication Data

US 2011/0025350 A1 Feb. 3, 2011

(51) Int. Cl.
*G01N 33/00* (2006.01)

(52) U.S. Cl.
USPC ............................................. 73/866; 324/679

(58) Field of Classification Search
USPC ............................................. 324/679; 73/866
See application file for complete search history.

(56) References Cited

U.S. PATENT DOCUMENTS

2004/0218440 A1* 11/2004 Kumar et al. ................. 365/202

OTHER PUBLICATIONS

Raj K. Gupta, Electronically Probed Measurements of Mems Geometries, Journal of Microelectromechanical Systems, Sep. 2000, pp. 380-389, vol. 9, No. 3, IEEE, USA.
Liwei Lin et al., A Micro Strain Gauge with Mechanical Amplifier, Journal of Microelectromechanical Systems, Dec. 1997, pp. 313-321, vol. 6, No. 4, IEEE, USA.
Peter M. Osterberg et al., M-Test: A Test Chip for Mems Material Property Measurement Using Electrostatically Actuated Test Structures, Journal of Microelectromechanical Systems, Jun. 1997, pp. 107-118, vol. 6, No. 2, IEEE, USA.
Jason Vaughn Clark, Electro Micro-Metrology, Dissertation Doctor of Philosophy in Applied Science and Technology, 2005, pp. 001-175, University of California, Berkeley, USA.
Jason Vaughn Clark, Electro Micro-Metrology, Dissertation Doctor of Philosophy in Applied Science and Technology, 2005, pp. 176-350, University of California, Berkeley, USA.
Jason Vaughn Clark, Electro Micro-Metrology, Dissertation Doctor of Philosophy in Applied Science and Technology, 2005, pp. 351-440, University of California, Berkeley, USA.
Jason Vaughn Clark, Electro Micro-Metrology, Dissertation Doctor of Philosophy in Applied Science and Technology, 2005, pp. 441-525, University of California, Berkeley, USA.
Jason Vaughn Clark, Electro Micro-Metrology, Dissertation Doctor of Philosophy in Applied Science and Technology, 2005, pp. 526-658, University of California, Berkeley, USA.
J. V. Clark et al., Practical Techniques for Measuring MEMS Properties, 2004, pp. 402-405, vol. 1, NSTI_Nanotech, USA.

* cited by examiner

*Primary Examiner* — Hezron E Williams
*Assistant Examiner* — Gregory J Redmann
(74) *Attorney, Agent, or Firm* — D'Hue Law; Cedric A. D'Hue; Stephen Farris

(57) ABSTRACT

This invention is a novel methodology for precision metrology, sensing, and actuation at the micro- and nano-scale. It is well-suited for micro- and nano-scale because it leverages off the electromechanical benefits of the scale. The invention makes use of electrical measurands of micro- or nano-scale devices to measure and characterize themselves, other devices, and whatever the devices subsequently interact with. By electronically measuring the change in capacitance, change in voltage, and/or resonance frequency of one or more test structures, a multitude of geometric, dynamic, and material properties may be extracted with a much higher accuracy and precision than conventional methods.

2 Claims, 15 Drawing Sheets

Sequence of Property Extractions

Level     Selected properties from electrical measurands

Level 1
If capacitance $\Delta C_i$ of lateral deflection is measured...
- a) Obtain overetch, $\frac{1}{2}\Delta w = \frac{1}{2}\Delta w(\Delta C_a, \Delta C_b)$
- b) Geometry i.e. widths, gaps, lengths, areas, volumes $(\Delta C_a, \Delta C_b)$
- i) Base compliance $K_{base} = K_{base}(\Delta C_a, \Delta C_b, \Delta C_c)$
- i) Web compliance $K_{web} = K_{web}(\Delta C_a, \Delta C_b, \Delta C_c)$
- c) Sidewall angle $\theta = \theta(\Delta C_a, \Delta C_b, \Delta C_c)$
- h) Layer thickness $h = h(\Delta C_a, \Delta C_b; \omega_\theta)$

Level 2
If ds-potential $\Delta V_{ds}$ & ds-capacitance $\Delta C_{ds}$ are included...
- a) Obtain comb-drive force $F_0 = F_0(\Delta C_a, \Delta C_b; \Delta V_{ds}, \Delta C_{ds})$
- c) Displacement $\Delta y_{ds} = \Delta y_{ds}(\Delta C_a, \Delta C_b; \Delta V_{ds}, \Delta C_{ds})$
- b) System stiffness $k_{sys} = k_{sys}(\Delta C_a, \Delta C_b; \Delta V_{ds}, \Delta C_{ds})$
- j) Beam stiffness $k_{beam} = k(\Delta C_a, \Delta C_b, \Delta C_c; \Delta V_{ds}, \Delta C_{ds})$
- k) Material Young's Modulus $E = E(\Delta C_a, \Delta C_b, \Delta C_c; \Delta V_{ds}, \Delta C_{ds})$
- m) Poisson's ratio $\nu = \nu(\Delta C_a, \Delta C_b, \Delta C_c; \Delta V_{ds}, \Delta C_{ds})$
- l) Shear modulus $G = G(\Delta C_a, \Delta C_b; \Delta V_{ds}, \Delta C_{ds}; \omega_\theta)$

Level 3
If resonances $\omega_r, \omega_0$ are included...
- a) Obtain damping factor $\gamma = \gamma(\omega_r, \omega_0)$
- b) Natural frequency $\omega_d = \omega_d(\omega_r, \omega_0)$
- g) Quality factor $Q = Q(\omega_r, \omega_0)$
- f) Material density $\rho = \rho(\Delta C_a, \Delta C_b; \Delta V_{ds}, \Delta C_{ds}; \omega_r, \omega_0)$
- d) System mass $m_{sys} = m_{sys}(\Delta C_a, \Delta C_b; \Delta V_{ds}, \Delta C_{ds}; \omega_r, \omega_0)$
- h) System elasticity $E_{sys} = E_{sys}(\Delta C_a, \Delta C_b; \Delta V_{ds}, \Delta C_{ds}; \omega_r, \omega_0; \omega_\theta)$
- e) System damping $d_{sys} = d_{sys}(\Delta C_a, \Delta C_b; \Delta V_{ds}, \Delta C_{ds}; \omega_r, \omega_0)$

Level 4
If capacitance of the stress-induced deflection is included...
- a) Strain $\varepsilon = \varepsilon(\Delta C_a, \Delta C_b; \Delta C_\sigma, \Delta C_{ds})$
- b) Obtain stress $\sigma = \sigma(\Delta C_a, \Delta C_b; \Delta C_\sigma, \Delta C_{ds})$
- c) Elongation & comb offset $\Delta y_\sigma = \Delta y_\sigma(\Delta C_a, \Delta C_b; \Delta C_\sigma, \Delta C_{ds})$

FIG. 1

Relative Magnitudes of Small Forces

| Force | Tangible Phenomena | Conventional Tools |
|---|---|---|
| $1\,N$ | Weight of Newton's apple | |
| $10^{-1}\,N$ | Translational force on a pitcher's curveball | |
| $10^{-2}\,N$ | Disk drive lift force | Mass balances |
| $10^{-3}\,N$ | Particulates in $1\,m^3$ of urban air | |
| $10^{-4}\,N$ | Indentations | |
| $10^{-5}\,N$ | Surface tension per centimeter of water | Nanoindenters |
| $10^{-6}\,N$ | Solar radiation per $m^2$ near earth | |
| $10^{-7}\,N$ | Exact force/length on a pair of 1 ampere wires $2m$ apart | Atomic force microscope |
| $10^{-8}\,N$ | Weight of a dust mite. Hydrogen per liter of water pH7. | |
| $10^{-9}\,N$ | Covalent bond. | |
| $10^{-10}\,N$ | Noncovalent bond. DNA rupture. | |
| $10^{-11}\,N$ | Gravitational force between two $1kg$ masses $1m$ apart | Magnetic resonance force microscope |
| $10^{-12}\,N$ | Light pressure $1mW$ laser pointer. Protein folding. | |
| $10^{-13}\,N$ | Casimir force / $\mu m^2$ on parallel plates with $1\mu m$ gap | Optical tweezers |
| $10^{-14}\,N$ | Weight of bacterium. Force of its brownian motion. | |
| $10^{-15}\,N$ | Resolution of optical tweezers | |
| $10^{-16}\,N$ | Force between a pair of electrons $1.5\mu m$ part | |
| $10^{-17}\,N$ | Resolution of magnetic force resonance force microscopy | |
| $10^{-18}\,N$ | Unpaired electron spins | |

FIG. 13

METHOD OF MEASURING MICRO- AND NANO-SCALE PROPERTIES

CROSS-REFERENCE TO RELATED APPLICATIONS

This application claims the benefit of provisional patent application Ser. No. 60/658,470, filed 2005 Mar. 3 by the present inventor.

FEDERALLY SPONSORED RESEARCH

Not Applicable

SEQUENCE LISTING OR PROGRAM

Not Applicable

BACKGROUND OF THE INVENTION

1. Field of Invention

This invention relates to the extraction of geometric, dynamic, and material properties, specifically to such properties which are used for the characterization of micro- and nano-scale systems.

2. Prior Art

Precise determination of geometric, dynamic, and material properties of micro- and nano-scale systems is fundamentally important to characterizing said systems. A precisely characterized micro/nanosystem becomes an accurate sensor and or actuator for the micro/nanotechnologist. Conventional metrology methods at this scale typically yield 1 to 3 significant digits of precision. Such low precision slows advancement in the field because researchers find it difficult to accurately measure and evaluate the new micro- and nano-scale phenomena. Precise metrology of micro- and nano-scale systems is vitally needed in order to fully exploit micro- and nanotechnology. In particular, precise test and characterization methods are required to: help understand the new physical phenomena at the micro- and nano-scale; help fabrication facilities define micro- and nano-scale material for potential users; facilitate consistent evaluations of material and process properties at the required scales; and provide a basis for comparisons among materials and systems fabricated at different facilities.

Micro- and nano-scale systems typically do not look like or behave like a designer originally predicts on paper or on computer. However, several microelectromechanical systems (MEMS) have achieved commercial success. A couple of examples are the accelerometers used in car airbags, and the micromirrors used in digital light processing projectors. Of the systems that have become useful, most (if not all) of their geometric and material properties remain uncertain during their lifecycle. The reasons include the following: many systems in use today have not required precise characterization due to their intentional lack of sensitivity to design parameters for robustness; if the effective mechanical performance is less than ideal, the performance may be improved by electronic tuning if an adequate characterization-reference exists; since conventional measurement techniques typically have large uncertainties associated with them, the engineer will receive a low return on the time and cost invested in performing the measurement.

The success of a few simple microdevices should not mask the need to develop more complex systems and to better understand, model, and predict more complex physical phenomena at the micro- and nano-scale. The prerequisites for said advancement are the precise characterization of the governing geometric, dynamic, and material properties which form the parameters of linear and nonlinear analytical models and numerical models. However, because of the above reasons, and because practical measurement techniques have been largely nonexistent for micro- and nano-scale systems, most researchers are reluctant to invest in the time and cost to measure the fundamental properties of their creations. Instead, many researchers have relied on the measured properties of similarly-processed materials that have been reported in the literature or they rely on the generic material property databases found in commercial MEMS software packages. Although the reported values found in the literature pertain to a particular processing sequence that is often repeated in other laboratories, variations that are inherent to current processing techniques make it difficult to exactly reproduce the results elsewhere. These resulting variations are due to many factors which stem from the dynamics of temperature, pressure, and concentration of the reactants during processing deposition and etching. Characterization of these dynamics continues to be an active area of research. Due to the current inability to precisely control these factors and the strong sensitivity of material properties on these factors, it is also difficult to reproduce exactly the same results on a subsequent run using the same equipment and recipe. What is more, during any particular run, material properties vary from wafer to wafer. And for each wafer on any run, material properties can vary over the wafer itself.

Although there are a multitude of conventional measurement methods, they are impractical and nearly all of the methods are relatively imprecise. Unlike the invention presented herein, conventional methods suffer from one or more of the following issues: the method is too costly for most budget-conscious organizations or institution; The methods are typically single-function; that is, it often requires the use of N distinct methods to extract N distinct properties; a large amount of chip real estate is required for methods which use a large array of test structures; The measurement is typically global and unable to extract local variations in properties; The extracted measurement is a function of one or more unconfirmed properties such that significant uncertainty remains; the measurement method itself is not well-characterized or well-calibrated, such that the extracted measurement typically yields about 1 to 3 significant digits of precision; the methods are time-consuming, which is not amenable to a pace of industry; there is a lack of characterization standards at this length scale, which makes it difficult for manufacturers to specify their materials and for customers to specify their needs; many methods are destructive, which may render the surround material unusable; many methods often require subjective interpretation which introduces human error into the overall uncertainty; nearly all measurement tools are relatively large and non-portable, which limits testing to suitable laboratory facilities; many methods are difficult to use and may require specialized personnel for their operation. In such cases, the precision of measurement depends on the expertise of the operator; nearly all conventional methods are difficult to automate, which is not amenable to the pace of industry; nearly all conventional characterization methods are performed in the laboratory before the system is packaged; such methods are not amenable to post-packed testing in-the-field when conditions change; and many test structures require unique fabrication processes, which limits such methods from being generally applied.

The characterization method of the present invention does not suffer from any of the aforementioned issues. The method should be contrasted to prior methods and tools. In particular, the present invention is most closely related to U.S. Pat. No. 6,542,829. In regards to the above issues, U.S. Pat. No. 6,542,829 is subject to issue Nos. 8, 9, 12, 13, and 14; that is, the method requires the purchase of costly software, it extracts geometrical properties only, the extracted measurements are functions of unconfirmed properties, the finite-element simulation is computationally intensive, and the uncertainty in the simulated result significantly affects the uncertainty of the extracted measurement. Other examples prior art include U.S. Pat. Nos. 6,998,851; 5,786,621; 6,753,528; 6,721,094; 6,567,715. An overview of conventional characterization methods may be found in "Electro Micro-Metrology" by Jason Vaughn Clark, Ph.D. dissertation, Dec. 20, 2005, pp. 583-605, and in the "MEMS Handbook, $2^{nd}$ Ed." edited by Mohamed Gad-el-Hak, Taylor and Francis, CRC Press, 2005.

In view of the foregoing, a need exists in the art for a practical and precise method to characterize micro- and nano-scale properties, which does not suffer from any of the aforementioned problems.

SUMMARY OF THE INVENTION

The present invention provides a practical method for precision metrology, sensing, and actuation at the micro- and nano-scale. The method is well-suited for the micro- and nano-scale because it leverages off the electromechanical benefits of the scale. The method uses micro- or nano-scale electromechanical test structures to measure and characterize themselves; characterize other devices that experience the same fabrication process. The calibrated devices may then be used as precise micro- and nano-scale sensors and actuators.

By electronically measuring the change in capacitance, change in voltage, and/or resonant frequency of just a few simple test structures, a multitude of geometric, dynamic, and material properties may be extracted with a much higher precision than conventional methods.

Examples of geometric properties include the extraction of: beam widths, beam lengths, gap spacing, etch hole size, plate area, sidewall angle, and layer thickness. Examples of dynamic properties include: comb drive force, minimum gap closing voltage, fringing field factor, displacement, system stiffness, displacement resonance, velocity resonance, natural frequency, damping factor, time constant, mass, and damping. And examples of material properties include: system Young's modulus, quality factor, beam stiffness, material Young's modulus, Poisson's ratio, shear modulus, residual strain, residual stress, and comb drive asymmetry.

High precision measurements are achieved by measuring all geometric, dynamic, and material properties as functions of precisely measured electrical measurands and exactly known layout parameters. The difference between layout and fabrication is a measure of the geometrical error. Since the geometric, dynamic, material properties are not all independent, only a few test structures and electrical measurands are all that is necessary to extract the multitude of properties.

The electrical measurands yield well-characterized uncertainties. For example, the last flickering digit of capacitance, voltage, or resonant frequency is a measure of the uncertainty. The electrical uncertainties include all internal and external noise sources. Since the uncertainties of all extracted properties are functions of the uncertainties of the electrical measurands; and since subsequent sensing or actuation is achieved by sensing or applying capacitance or voltage, then the uncertainty of the extracted properties are a measure of the practical limit of the precision. Capacitance is the most sensitive type of electromechanical sensing to date. For instance, capacitive changes on the order of zeptoFarads due to the deflection of micro-scale structures that have displaced a few femtometers have been achieved.

These and other advantages are achieved in accordance with the present invention as described in detail below.

BRIEF DESCRIPTION OF FIGURES

FIG. 1 provides a preferred sequence of parameter extraction.

FIG. 13 provides a sense of force magnitudes.

DETAILED DESCRIPTION OF PREFERRED EMBODIMENT

A preferred embodiment of the present invention is discussed below with reference to the accompanying drawings. It will be obvious to those skilled in the art that the present invention is not limited to the specific details and may be practiced with various modification, omissions, and additions thereto.

FIG. 1 generally illustrates a preferred method of property extraction in terms of a sequence of levels distinguished the type of electrical measurement. The method determines a multitude of geometric, dynamic, and material properties as functions of electrical measurands.

The first level in the sequence of property extractions corresponds to the properties that are functions of changes in capacitance. The second level in this sequence corresponds to properties that are functions of changes in voltage and changes in capacitance due to a prescribed displacement, and the electrical measurands from the previous level. The third level in this sequence corresponds to properties that are functions of displacement resonant frequencies, velocity resonant frequencies, and the electrical measurands from the previous level. The final level corresponds to properties that are functions of stress-induced changes in capacitance and the electrical measurands of the previous levels.

The first level is the preferred method to extract geometric properties. The geometric properties comprise overcut, widths, gaps, lengths, sidewall angles, thicknesses; that is, areas, volumes, and distances between structures. Base and web compliances are also determined as this level.

The second level is the preferred method for the extraction of properties that comprise comb drive force, displacement, system stiffness, beam stiffness, material Young's modulus, Poisson's ratio, and shear modulus.

The third level is the preferred method for the extraction of dynamic properties that comprise damping factor, natural frequency, quality factor, material density, system mass, and system damping.

The fourth level is the preferred method for the extraction of properties comprising strain, stress, and elongation.

Figure 2:
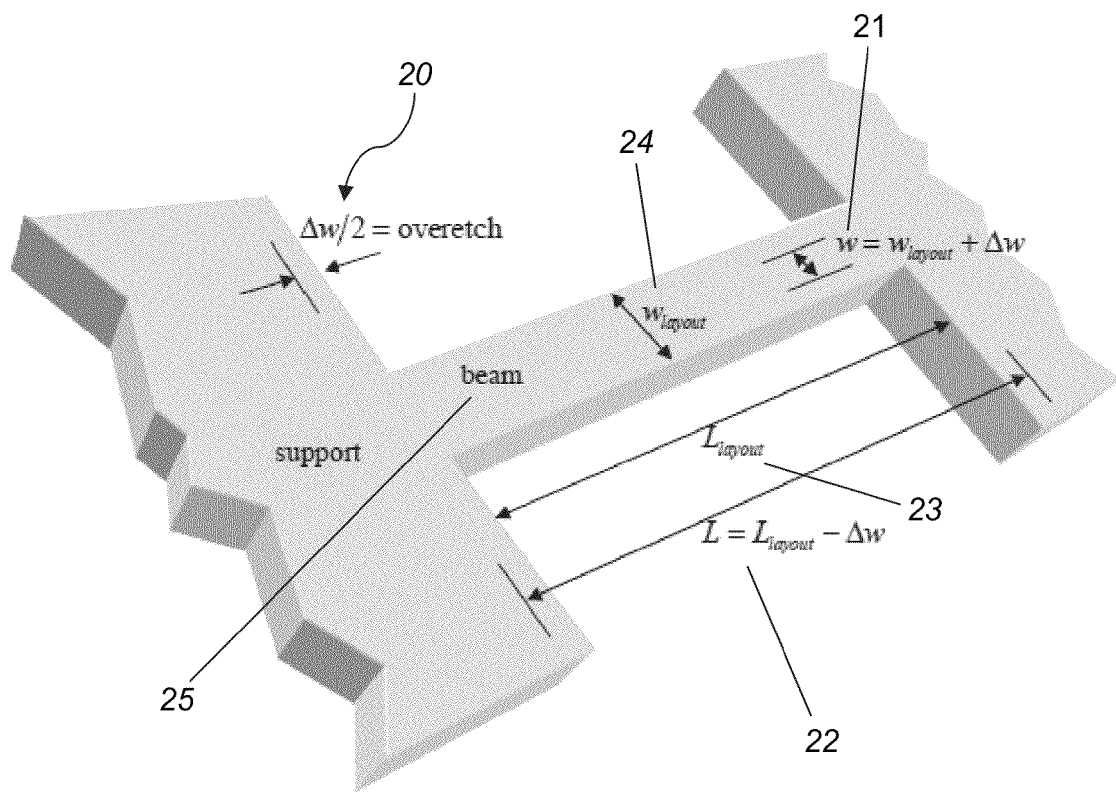
FIG. 2 depicts the effect of overcut.

The fabricated properties of a device are often significantly different than predicted. FIG. 2 shows the geometrical effect of overcut 20 on width 21 and length 22 of a beam 25. Overcut is defined as one half of the difference in width between layout and fabrication. Here, a negative overcut value decreases the width while increasing the length. Depending on the nature of the process, overcut may be effectively due to processes unrelated to etching, such as optical misalignments, etc. Overcut may be a positive or negative quantity. We assume that the overcut value is consistent for the entire geometry of this test case. The desired width 24 and length 23 from layout are shown. Variation in geometry may significantly other properties, for example, stiffness, and resonant frequency.

Figure 3:
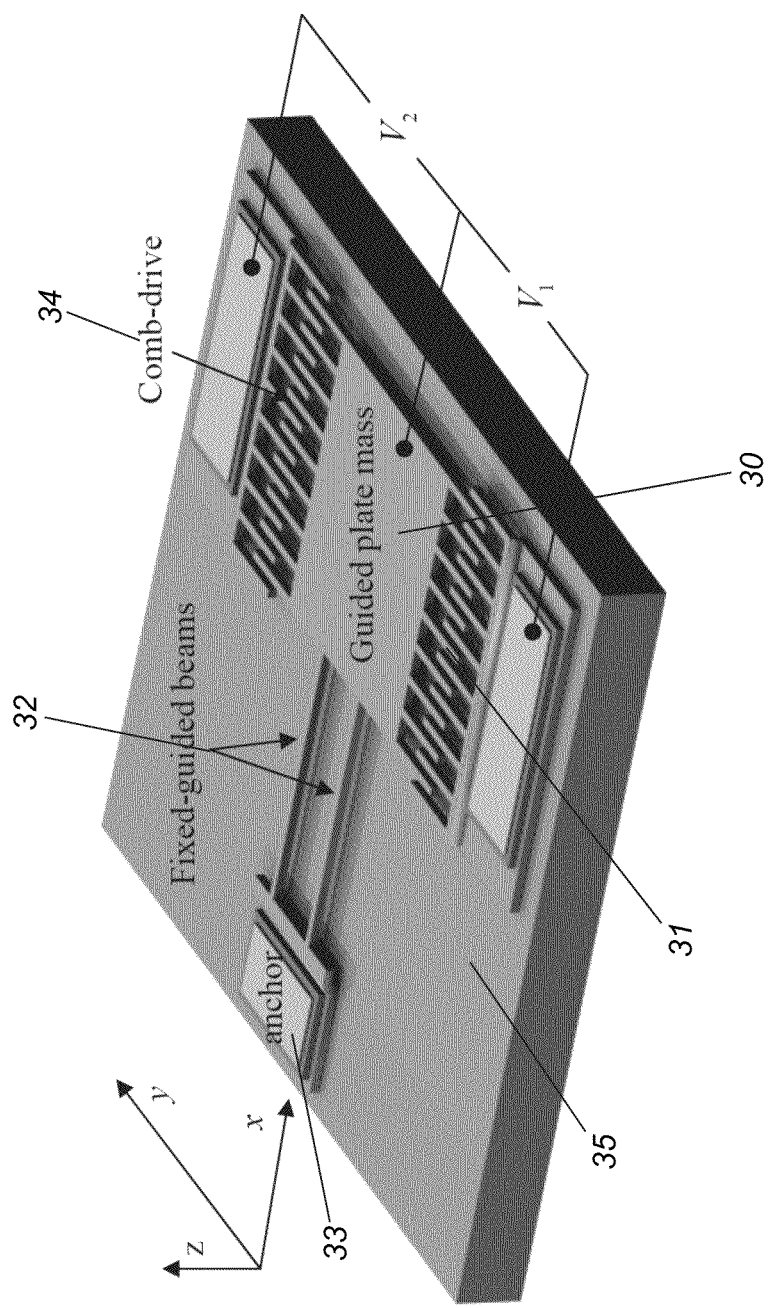
FIG. 3 depicts a basic test structure.

A preferred test structure is shown in FIG. 3. The test structure consists of a pair of fixed-guided beams 32 attached to a plate mass 30. The plate mass has a pair of differential comb-drive actuators 31, 34 which laterally deflect or resonate the device. The moveable structure is anchored 33 to the substrate 35. The model of this system is composed of inertial, damping, stiffness, and excitation components. The mass of the one-dimensional system includes the mass of the plate, comb-fingers, and flexible beams. The stiffness of the system includes the beams along with the compliant beam-to-anchor and beam-to-plate interfaces. The damping of the system includes viscous damping due to the movement of the plate, the comb-fingers, and the flexible beams. The two parallel fixed-guided beams prevent rotation of the plate mass.

Figure 4:
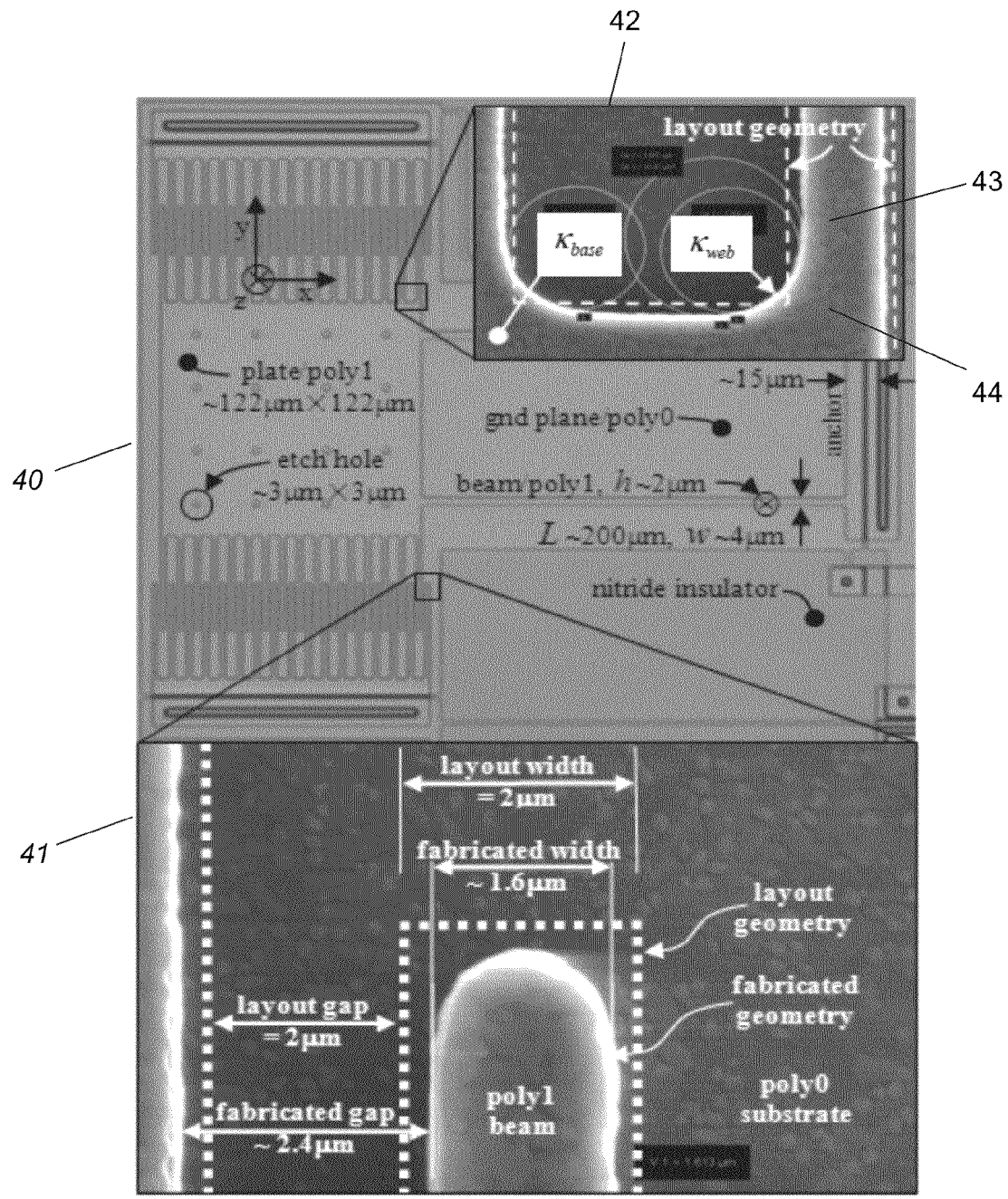
FIG. 4 shows optical and scanning electron microscopic images of a preferred test structure.

Optical 40 and scanning electron microscope 41, 42 images of a test structure is shown in FIG. 4. The scanning electron microscope images 41, 42 are magnifications of the optical image. These magnifications are of a comb drive finger 43 and finger-to-support attachment 44. The superimposed dashed lines in 41 and 42 indicate the desired geometry of the designer. Instead of flat sidewalls, the sidewalls are coarse.

Figure 5:
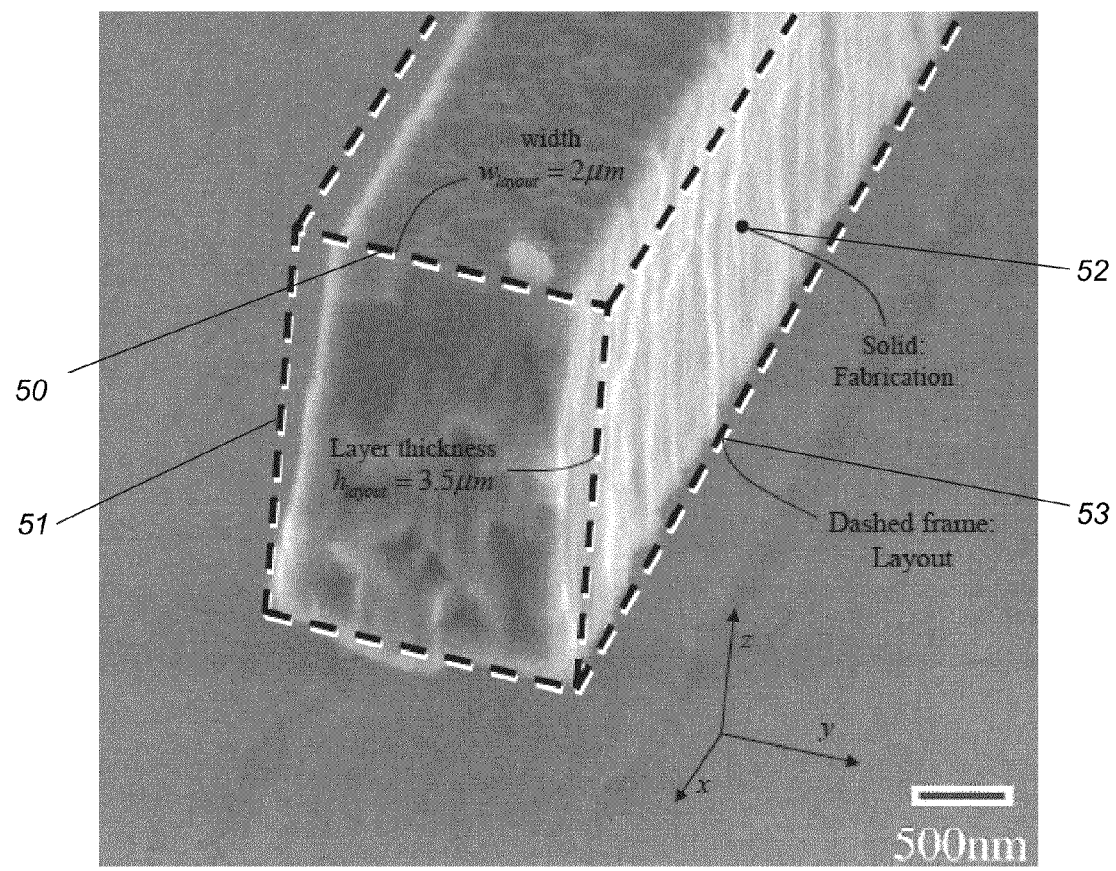
FIGS. 5 and 6 show the variation in geometry of a fabricated beam.
Figure 6:
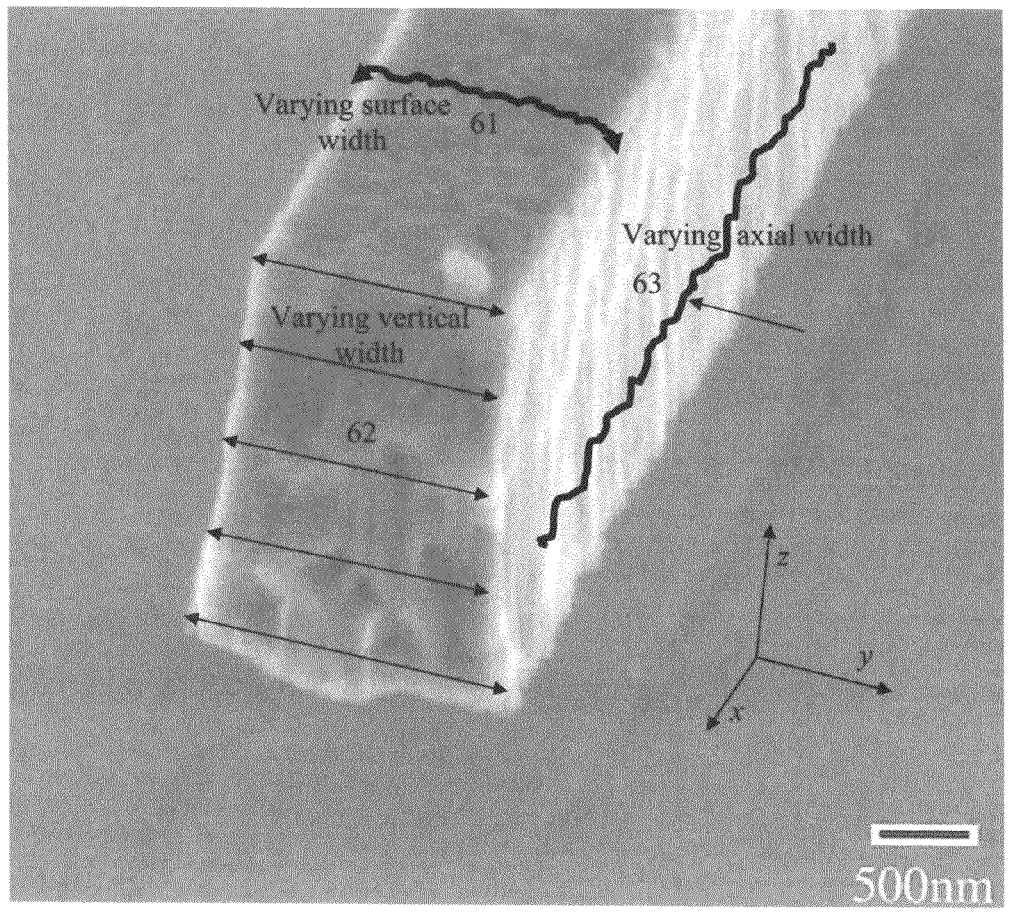

A cross sectional view of a fabricated beam is shown in FIG. 5. The superimposed outline 53 indicates the desired geometry. The desired width 50 and layer thickness 51 are significantly different than the fabricated result 52. Profiles of variations in width of a polycrystalline silicon beam are shown in FIG. 6, as viewed by: 61 top surface profilometry; 61 tensile fracture and scanning electron microscopy; and 63 sidewall surface profilometry. Method 61 provides a measure of local, top width only. Global measurement, raster-scanned over the entire top surface, is doable but extremely time consuming. However, beam widths which vary along the z-axis are not considered. Method 62 includes the variation of width along the z-axis but ignores the variation of width along the x-axis of the beam. Method 63 includes both the variation of beam width along the beam's x-axis and z-axis. However, sidewall profilometry has yet to be realized. It can be shown that a width that would be obtained by averaging the variations in width obtained from sidewall profilometry does not produce the correct effective width. Therefore, much more detailed structural analysis of the sidewall contour would be necessary if method 63 became a practical reality.

Figure 7:
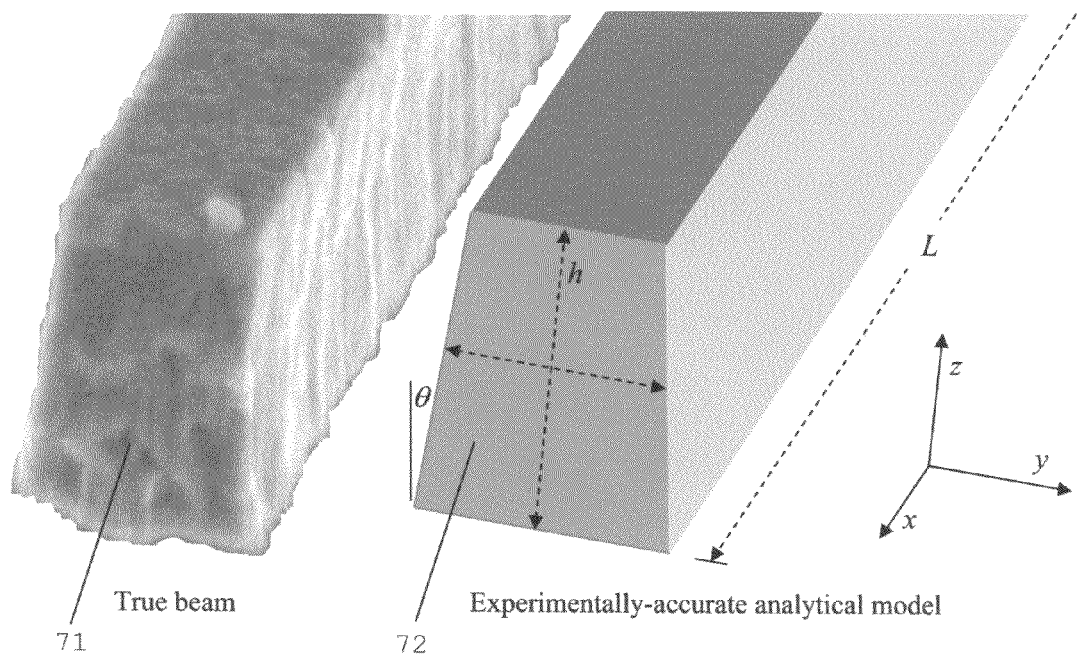
FIG. 7 compares the fabricated geometry with its model.

An experimentally-accurate model of a beam is depicted with its fabricated counterpart in FIG. 7. This figure visually exemplifies the concept of experimentally-accurate geometrical extraction. The beam on the left shows an angled cross section of the fabricated beam 71. The cantilever on the right 72 is an idealized representation of the cantilever on the left. The geometrical parameters of the idealized representation, namely beam width w, beam length L, sidewall angle θ, and layer thickness h, are chosen such that the analytical performance of the idealized model precisely matches the experimental performance of the true fabricated beam. Hence, we say that the idealized beam is experimentally accurate. This implies that the effective stiffness of the analytical model precisely matches the effective stiffness of the true beam such that the analytical deflection at the end of the beam precisely matches the experimental deflection. In essence, the precision of the analytical model effectively becomes the precision of experimental detection, which we call the practical limit. This methodology is a substantial improvement over conventional methods where model parameters are not accurately verified. The geometrical parameters (w, L, θ, h) are determined from performance instead of measured directly. If geometry is measured directly, then errors in geometry propagate into significant performance errors; however, by matching performance instead, we obtain the suitable geometry at once. This methodology increases the accuracy of geometrical parameters and it allows models to achieve much more accurate simulation results.

Figure 8:
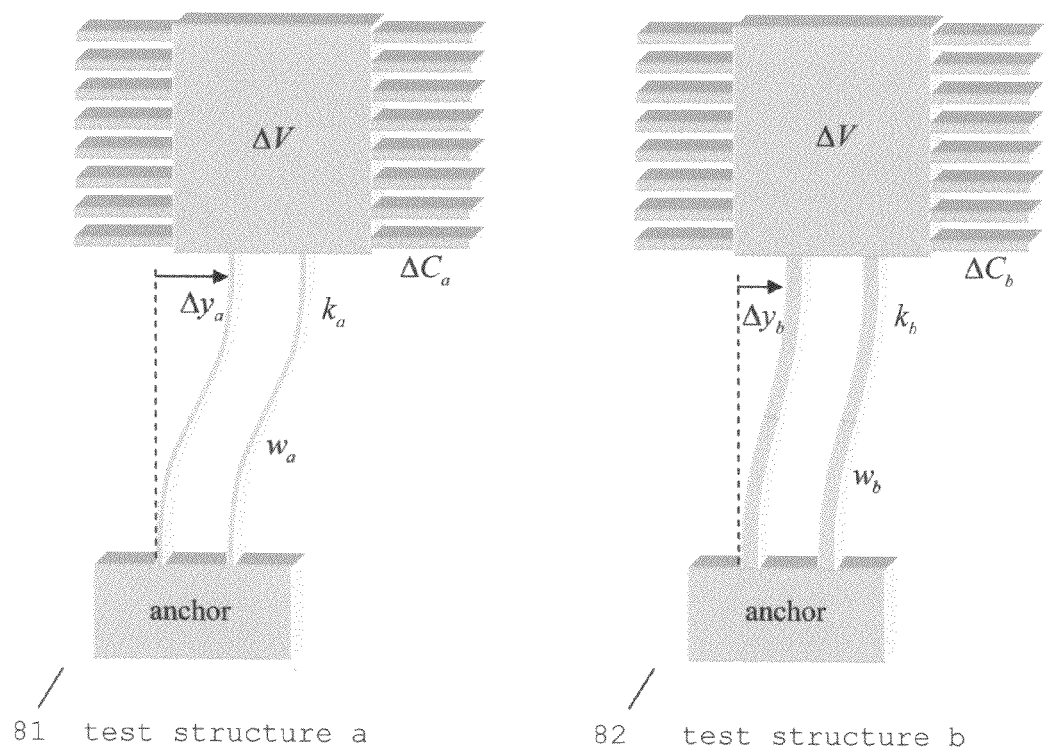
FIG. 8 depicts actuated states of two test structures.

Actuation of the comb drive causes deflection, which produces a change in capacitance. Depictions of actuated states of two test structures are shown in FIG. 8. The layout widths of the support beams of test structure b 82 are a factor of $n_b$ greater than the support beams of test structure a 81. Since $w_b > w_a$ then the stiffness of test structure b is greater than that of a: $k_b > k_a$; the change in capacitance and displacement are less: $\Delta C_a > \Delta C_b$, $\Delta y_a > \Delta y_b$; but the applied forces are equal ($F_a = F_b$) since the fabricated comb drives are assumed to have identical errors. The fabricated comb drives are assumed to be identical. If the comb drives are operating within their linear operating range then the ratios of their capacitance to displacement are assumed to be identical, $\Delta C_a / \Delta y_a = \Delta C_b / \Delta y_b$. Since material properties and actuation forces between the two test structures are initially unknown but identical, these terms cancel out by division, and the geometrical error $\Delta w$ is solved as a function change in capacitance. Geometrical error is the difference between a layout and fabrication dimension.

Figure 9:
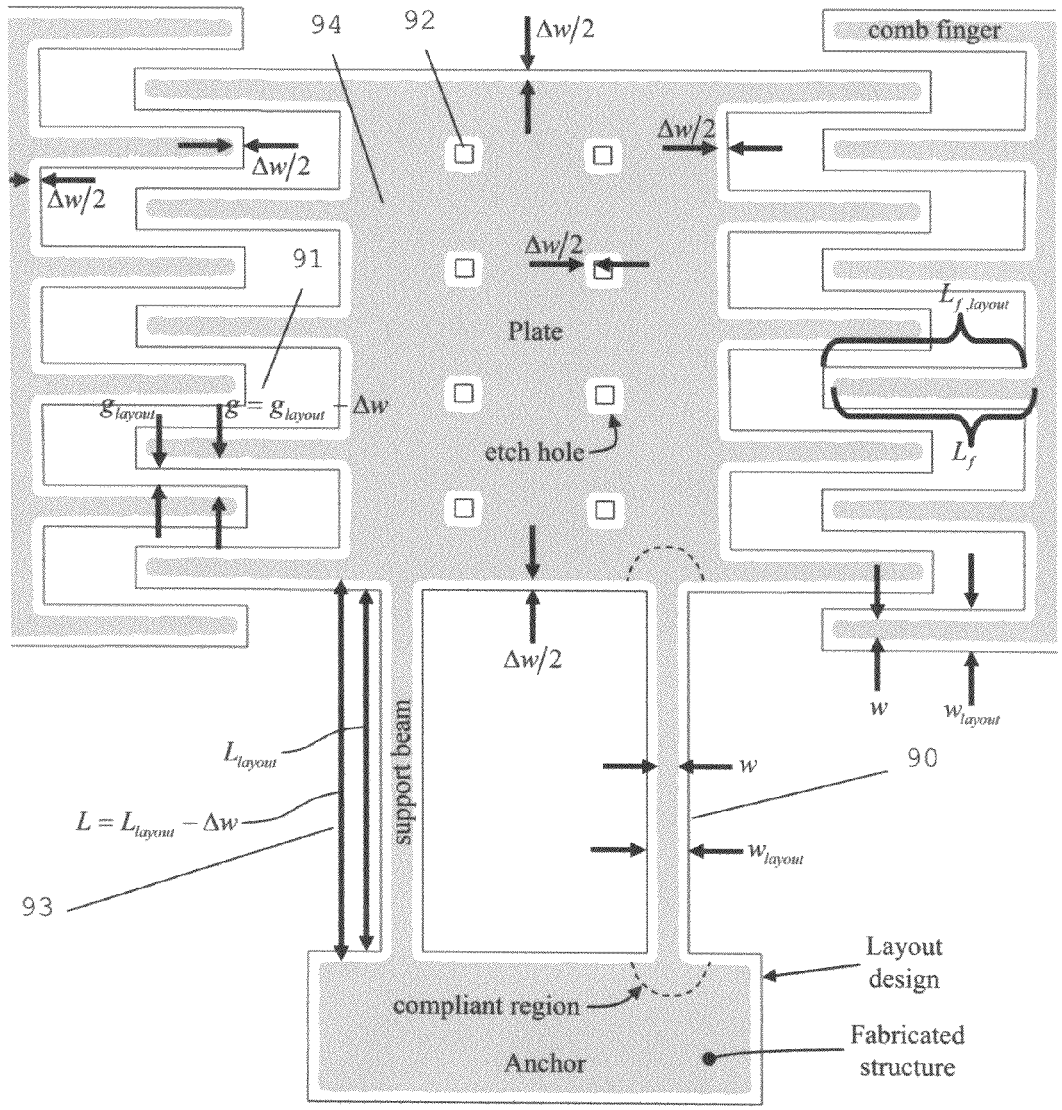
FIG. 9 compares the fabricated geometry to layout geometry.

Upon the measurement of geometrical error $\Delta w$ a multitude of other dimensions become available at once. FIG. 9 shows that the all beam widths 90, gaps 91 between structural elements, etch holes 92, lengths 93, and areas 94 are all functions of geometrical error $\Delta w$, which is a function of change in capacitance. The fabrication error is locally consistent if the elements are subject to the same deposition and etch processes.

Figure 10:
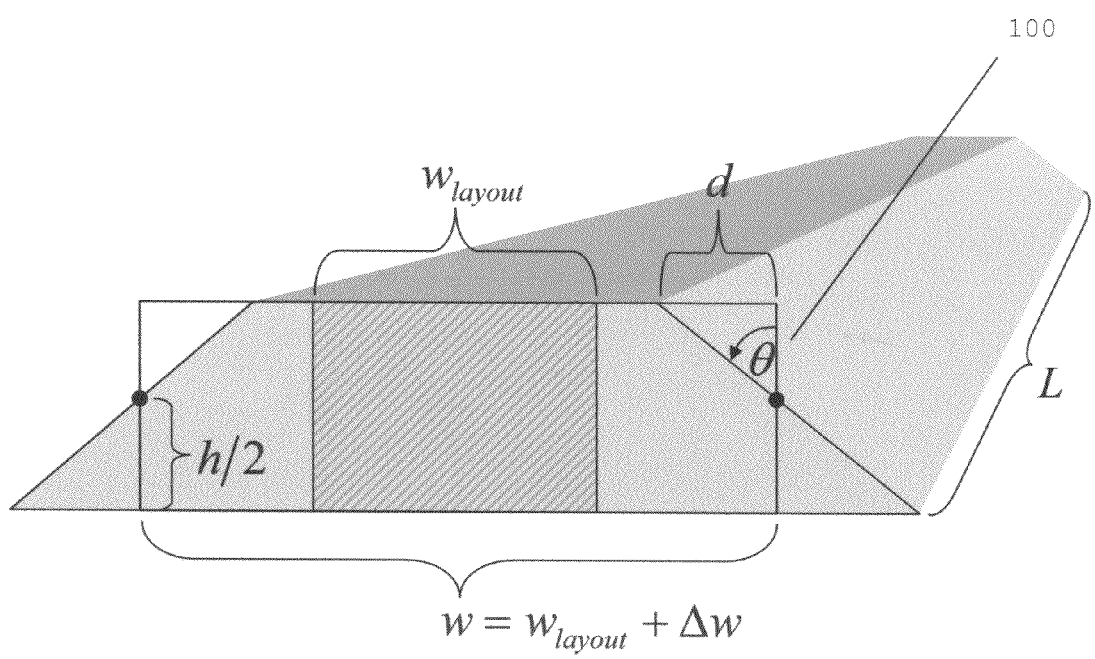
FIG. 10 depicts the geometry of a trapezoidal cross section of a beam.

The Geometry of the trapezoidal beam is shown in FIG. 10. The "hatched" cross section represents the cross section that would be obtained if fabrication produced vertical sidewalls and no beam width error. However, fabrication inaccuracies offset beam widths by $\Delta w$ and offset sidewalls from the vertical by θ 100. For structures with such trapezoidal cross sections, an additional test structure with a unique support beam width is required.

Figure 11:
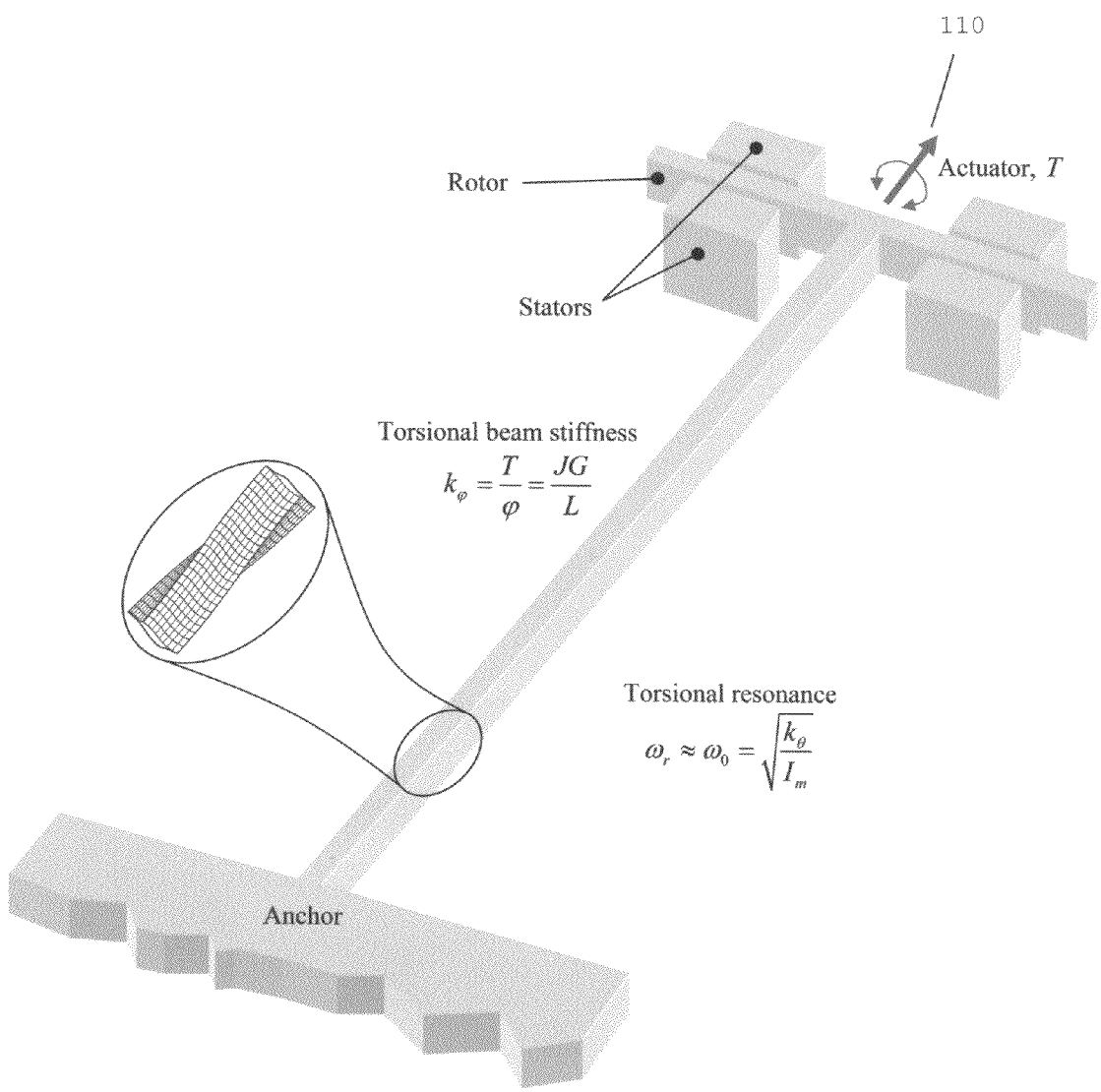
FIG. 11 depicts of a torsional resonator test structure for the determination of layer thickness.

Measurement of layer thickness is extracted by using a torsional test structure. A depiction of a torsional resonator test structure is given in FIG. 11. The device operates by exciting the first torsional resonant mode wr by periodically pumping the electrostatic actuator at this frequency. The electrostatic actuator applies a small torque T 110 at the free end of the cantilever by taking advantage of asymmetries about the structural plane. It is necessary that the torsional resonant frequency is not close to any other resonant modes, such as lateral modes. Since the vertically-projected area of the comb fingers is small, squeeze-film damping between the comb fingers and ground plane is insignificant. The small Couette damping between the opposing sidewall surface areas of the comb fingers and stators is the dominate source of damping.

Figure 12:
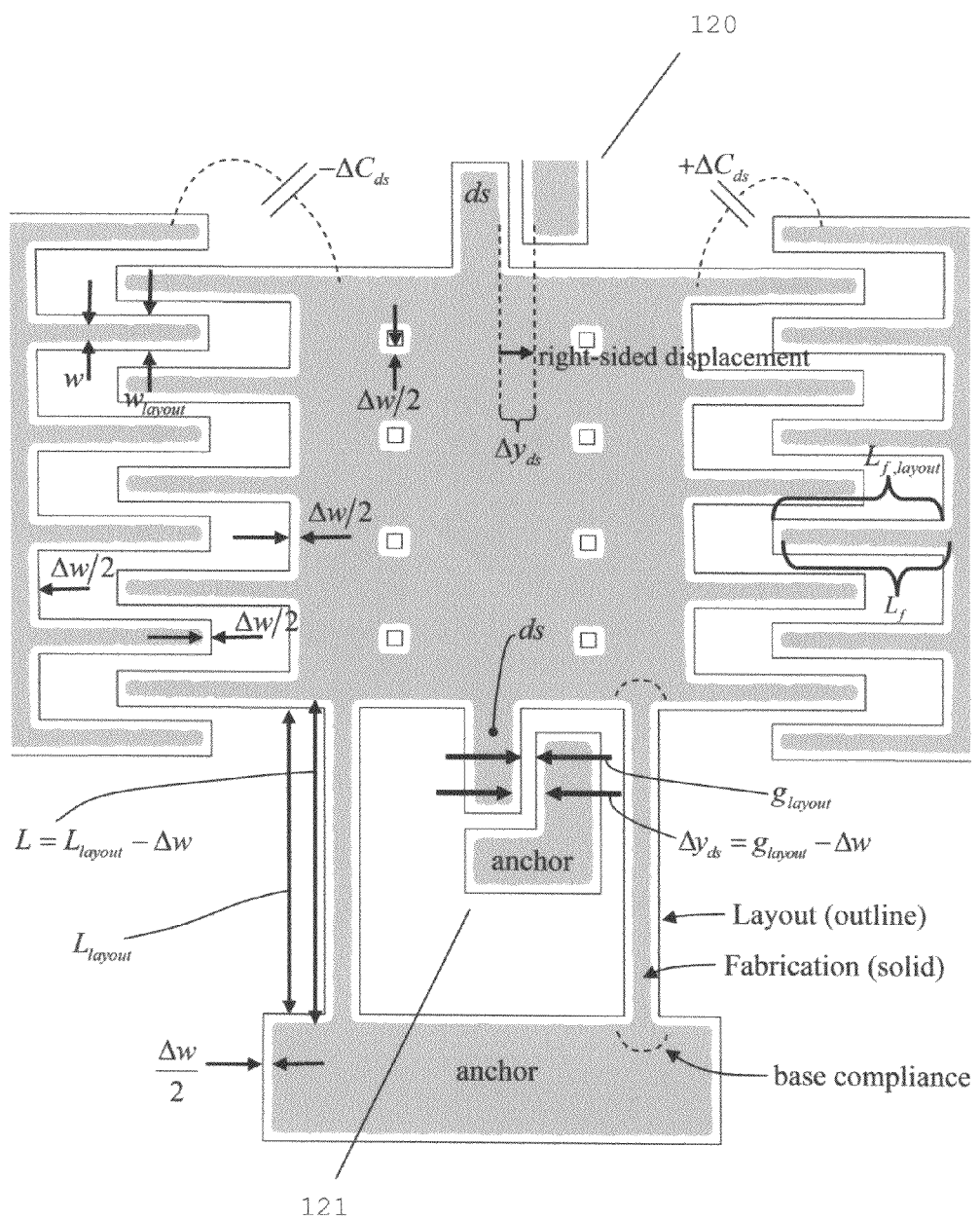
FIG. 12 depicts a test structure with displacement stops.

A test structure with displacement stops 120 is depicted in FIG. 12. This depiction shows the fabricated (solid) versus layout (outline) geometry of the basic test structure with displacement stops located by the upper and lower sides of the plate mass 121. If the overcut is known, then the size of the displacement stop is $\Delta y_{ds} = g_{layout} - \Delta w$. The displacement stop is used to create a known displacement.

Upon closure of the displacement stop gap, a known displacement has been traversed, which produces a change in capacitance. This ratio of change in capacitance to displacement is a constant for a given comb drive operating in its linear regime. This ratio is proportional to the force generated by the comb drive. The proportionality factor is half of the applied voltage squared. Relative magnitudes of force are provided in FIG. 13. The resolution in force (as with other properties) is determined by the resolution by the electrical measurands it is cast as a function of electrical measurands.

Figure 14:
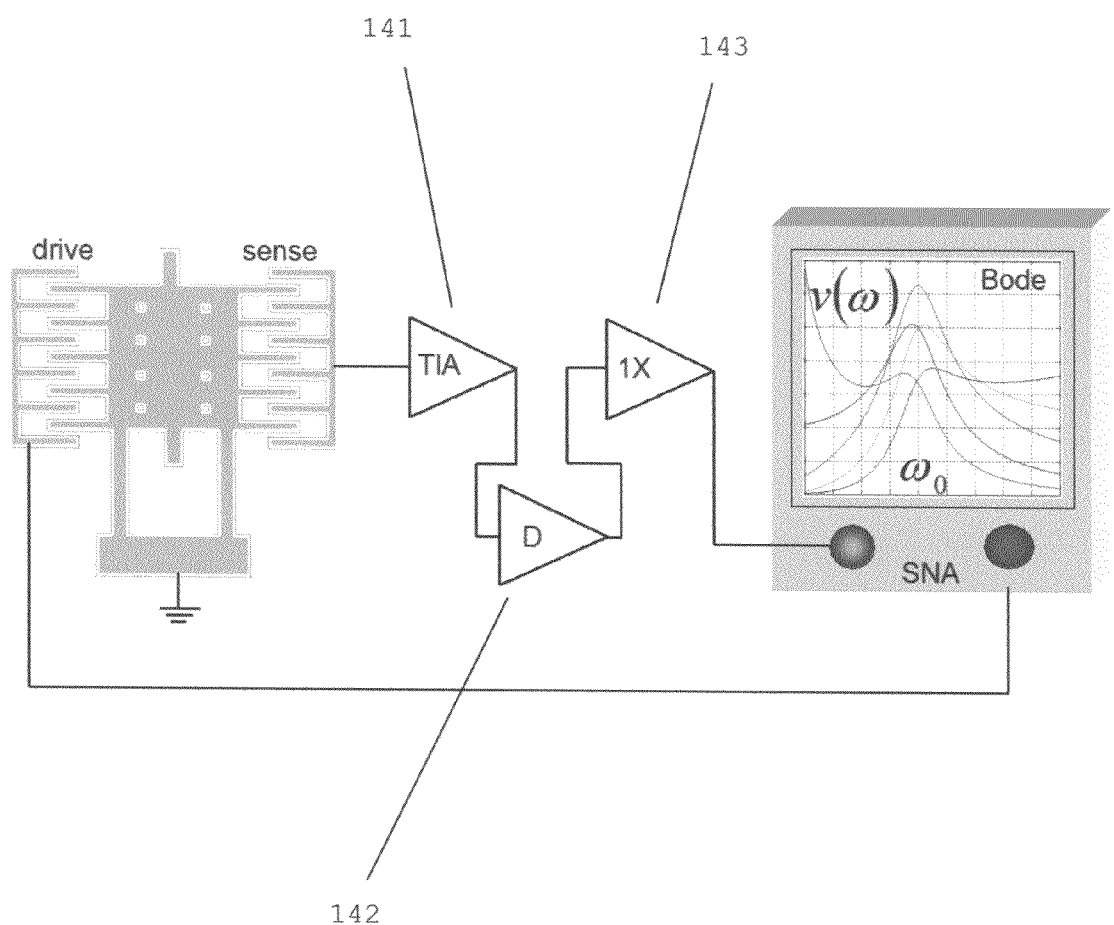
FIG. 14 shows a preferred method to extract velocity resonance.

An experimental setup for measuring velocity resonance is depicted in FIG. 14. A trans-impedance amplifier 141 amplifies the sensor signal, which is filtered and differentiated 142 and buffered 143. The final output of the resonating test structure is a time derivative of its input. The frequency which maximizes this differentiated signal is the velocity resonant frequency in a damped environment, which is identical to displacement resonant frequency in vacuum.

Figure 15:
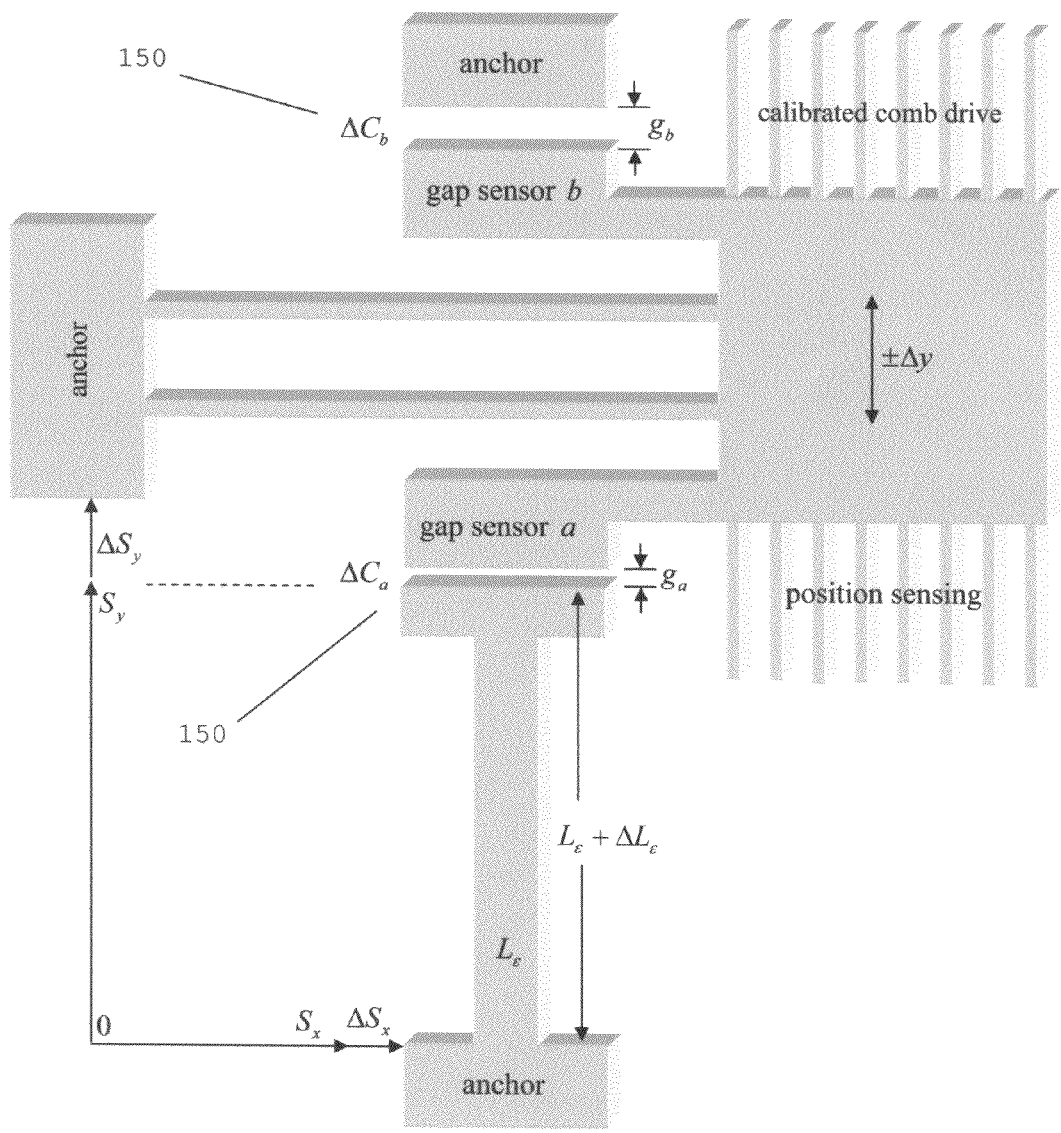
FIG. 15 depicts a strain sensor.

A strain sensor is depicted in FIG. 15. Such a design may be used to sense 1) residual strain in the material or 2) strain in the underlying substrate. If strain is zero, the two gaps, 150 and 151, are equal $g_a = g_b$. If strain is not zero, then 150 is not equal to 151, i.e. $g_a \neq g_b$. This is because residual strain in the structural material produces elongation of the beam labeled $L_e$, which produces a change $-\Delta L$ in the electrostatic gap $g_a = g_b - \Delta L$. For strain due to the substrate, substrate strain $\Delta S/S$ produces a similar change in the gap by causing a change in the positions of the anchors with respect to each other. E.g. the anchor at substrate coordinate (0,S) may strain to (0,$S_x$ y $S+S_y$, which produces an identical change $\Delta S_y$ in gap $g_a = g_b + \Delta S_y$. If strain exists, the gaps will not be equal. The difference in size of the gaps 150 and 151 can be determined by the electrostatic pull-in phenomenon. That is, the smaller gap will pull in at a lower applied voltage than the larger gap.

Advantages

From the descriptions given above, a number of advantages of the present invention become evident:

a) The method is inexpensive. Its low cost should appeal to most organizations, institutions, or individuals such as university researchers and classroom laboratories, start-up companies, high schools, or individuals. Conventional methods typically require the budget of governmental agencies or large industrial companies.

b) The method is accurate. The accuracy is determined by the precision of the electrical measurand parameters. For example, capacitance is the most precise electrical measurand to date. Conventional methods are typically have a very low number of significant digits of precision.

c) The method is efficient. Over two-dozen properties can be extracted with just a one or more test structures and electrical measurements. Conventional metrology apparatuses yield much less, typically only one property.

d) Since only one or a few test structures are required, only a small amount of chip real estate is required for characterization. Conventional techniques typically require a chip's worth of test structures.

e) Since only a small test area is required, the measurement is localized. Conventional techniques typically measure global properties, and are unable to extract local variations in properties.

f) Since the extracted measurement is a function well-understood electrical measurands, then the uncertainty in the extracted property is well-defined. Conventional methods typically leave one or more parameters unconfirmed or with a large uncertainty.

g) The method is well-characterized since it characterizes itself. Conventional methods are typically not as well-characterized or as well-calibrated since they rely on another method (which has a higher precision) to calibrate them.

h) The method is fast. Conventional methods are typically time-consuming, which can be costly.

i) The method is performance-based. Since the performance is a much more tangible measurement which can be used to measure material properties, then a standardization of micro- and nano-scale metrology can be realized. Currently, there is a lack of characterization standards at this length scale, which makes it difficult for manufacturers to specify their materials and for customers to specify their needs.

j) The method is non-destructive. Many conventional methods are destructive.

k) The method does not require visual or other subjective interpretation. Many conventional methods require subjective interpretation, which introduces human error into the overall uncertainty.

l) The method is lightweight and portable. Since the method only requires a small amount of chip real estate, the method may be packaged alongside a primary device. The primary device may require periodic characterization, or characterization may be required after long dormancy or after a significant environmental change. Nearly all conventional measurement tools are relatively large and non-portable, which limits their usage to suitable laboratory facilities.

m) The method is easy to use. Many conventional methods are difficult to use and require specialized personnel for their operation. In such cases, the precision of measurement depends on the expertise of the operator.

n) The method is automatable. Such a feature is attractive to batch-fabricated processes of mass production. Nearly all conventional methods are difficult to automate, which is not amenable to mass production.

o) The method can be applied to virtually all fabrication processes. Most conventional methods require unique fabrication processes, which limits their utility.

Those skilled in the art will realize that each of the aforementioned advantages is a much-needed and vertical advancement in characterization at the micro- and nano-scale.

What is claimed is:

1. A method of using electrical measurands to analyze and characterize mechanical properties of micro- and nano-scale electromechanical systems, wherein electrical measurands include capacitance, voltage, or current, wherein the mechanical properties include geometric, dynamic, or material properties, wherein the geometric properties include in-plane and out-of-plane dimensions of a fabricated structure, wherein dynamic properties include displacement, velocity, acceleration, mass, damping, stiffness, force, pressure, or temperature, wherein material properties include Young's modulus, stress, strain, density, Poisson's ratio, viscosity, thermo-elasticity, or thermal-conductivity, wherein electrical measurands are used to extract mechanical properties of one or more micro/nano electromechanical systems, comprising the steps of:

a. means of determining the architecture of one or more test structures having an architecture emulating said given architectural properties and exhibiting a predetermined layout;
b. means of co-producing said micro/nano electromechanical structure with said test structures as a unitary device;
c. means of measuring the geometric, dynamic and material properties of the micro/nano electromechanical system by correlating said predetermined layout and performance to electrical-based sensing and actuation to determine said properties and associated errors;
d. means of calculating one or more changes in capacitances of one or more micro/nano electromechanical systems i due to deflection including obtaining geometry overcut as function of changes in capacitances;
e. means of using overcut and layout geometry to calculate geometry comprising widths, gaps, lengths, areas, and volumes as functions of changes in capacitances;
f. means of calculating compliances Kbase and Kweb as functions of changes in capacitances;
g. means of calculating sidewall angle $\theta$ as a function of changes in capacitances;
h. means of calculating layer thickness h as a function of changes in capacitances and torsional resonance;
i. means of calculating one or more displacement-stop potentials and corresponding changes in capacitances of said test structure;
j. means of calculating a sensed or applied comb-drive force F as a function of changes in capacitances and applied voltages;\
k. means of calculating displacement as a function of changes in capacitances and applied voltages;
l. means of calculating system stiffness as a function of changes in capacitances and applied voltages;
m. means of calculating beam stiffness as a function of changes in capacitances and applied voltages;
n. means of calculating material Young's modulus E as a function of changes in capacitances and applied voltages;
o. means of calculating Poisson's ratio as a function of changes in capacitances and applied voltages;
p. means of calculating shear modulus as a function of changes in capacitances and applied voltages;
q. means of calculation damping factor as a function of displacement resonance and velocity resonance;
r. means of calculating natural frequency as a function of displacement resonance and velocity resonance;
s. means of calculating quality factor as a function of displacement and velocity resonances;
t. means of calculating material density as a function of said electronic measurands changes in sensed capacitances, applied voltages, and resonance frequencies;
u. means of calculating system mass as a function of said electronic measurands, changes in sensed capacitances, applied voltages, and resonance frequencies;
v. means of calculating system elasticity as a function of changes in sensed capacitances, applied voltages, and resonance frequencies;
w. means of calculating system damping as a function of changes in sensed capacitances, applied voltages, and resonance frequencies;
x. means of measuring the change in capacitance of the stress-induced deflection;
y. means of calculating strain as a function of changes in sensed capacitances;
z. means of calculating stress as a function of changes in sensed capacitances;
aa. means of calculating elongation comb offset as a function of changes in sensed capacitances; and
bb. means of calculating displacement as a function of changes in sensed capacitances.

2. The method of claim 1 wherein the uncertainties of said properties are functions of the uncertainties of said electrical measurands comprising capacitance, voltage, current, and or resonance frequencies.

* * * * *